United States Patent [19]

Coburn

[11] 4,028,154

[45] June 7, 1977

[54] AMMONIUM 2,4,5-TRINITROIMIDAZOLE

[75] Inventor: Michael D. Coburn, Los Alamos, N. Mex.

[73] Assignee: The United States of America as represented by the United States Energy Research and Development Administration, Washington, D.C.

[22] Filed: Sept. 1, 1976

[21] Appl. No.: 719,636

[52] U.S. Cl. .................................. 149/92; 260/309
[51] Int. Cl.² ........................................ C06B 25/34
[58] Field of Search ...................... 149/92; 260/309

[56] References Cited

UNITED STATES PATENTS 3,898,112   8/1975   Strecker et al. ................. 149/92 X

OTHER PUBLICATIONS

Novikov et al., "Nitration of Imidazoles with Various Nitrating Agents," Khim. Geterosikl. Soedin., vol. 6, p. 503 (1970).

*Primary Examiner*—Leland A. Sebastian
*Attorney, Agent, or Firm*—Dean E. Carlson; Edward C. Walterscheid

[57] ABSTRACT

The chemical explosive, ammonium 2,4,5-trinitroimidazole, has explosive performance comparable to that of the well-known RDX, but a thermal stability which is significantly greater.

1 Claim, No Drawings

AMMONIUM 2,4,5-TRINITROIMIDAZOLE

BACKGROUND OF THE INVENTION

The invention described herein relates to chemical explosives having good thermal stability.

In modern ordnance there is a strong requirement for explosives having both good thermal stability and good explosive power. In the various explosives taught in the prior art, these two requirements are somewhat mutually exclusive. That is to say, those explosives having good thermal stability exhibit poorer explosive performance and vice versa.

The compound 2,4,5-trinitroimidazole is known in the literature as are its potassium and imidazole salts. See Novikov et al., "Nitration of Imidazoles with Various Nitrating Agents," Khim. Geterosikl. Soedin., vol. 6, p. 503 (1970). There is nothing in the literature, however, which in any way suggests either any explosive properties or the thermal stability of the parent compound or the potassium or imidazole salts.

SUMMARY OF THE INVENTION

I have found that the compound ammonium 2,4,5-trinitroimidazole has an explosive performance comparable to that of the well-known RDX, but a thermal stability which is significantly better. While the thermal stability of the ammonium 2,4,5-trinitroimidazole is similar to that of the potassium salt, its explosive performance is substantially better. The reason for this is believed to be that adding the elements of ammonia to trinitroimidazole provides hydrogen so that more water is formed in the detonation. This is desirable in that the lower the molecular weight of the detonation products, the higher the Chapman-Jouguet pressure. But in the case of the potassium salt, which contains no hydrogen, only $CO_2$ and perhaps some CO is formed. The potassium contributes nothing but dead weight. The imidazole salt, which is the only other salt reported, is so poorly balanced that it is a low-order explosive at best.

DESCRIPTION OF THE PREFERRED EMBODIMENT

Ammonium trinitroimidazole is readily prepared by treating an ether solution of 2,4,5-trinitroimidazole with anhydrous ammonia. By way of example, a solution of 2,4,5-trinitroimidazole (0.01 mol) in anhydrous ether (50 cm$^3$) was saturated with anhydrous ammonia at 0°–5° C. The precipitated solid which resulted was collected by filtration, washed with ether, and dried in an oven at 80° C to yield 20.5 g (91%) of ammonium 2,4,5-trinitromidazole, which was purified by recrystallization from ethyl acetate.

Anal. Calc. for $C_3H_4N_6O_6$: C, 16.37; H, 1.83; N, 38.18. Found: C, 16.25; H, 2.07; N, 38.26.

The ammonium 2,4,5-trinitroimidazole produced in accordance with the foregoing method has the following characteristics:

Melting Point — 248° C
Differential Thermal Analysis — Stable to 248° C
Vacuum Stability — 4.4 cm$^3$/g/48 h at 200° C; 5.4 cm$^3$/g/29 days at 175° C
Impact Sensitivity (Type 12) — 50.3 cm
Crystal Density — 1.835 g/cm$^3$
Heat of Formation ($\Delta f^\circ$) — −86.02 KJ/mol
Detonation Velocity (calc) — 8560 m/s
C-J Pressure (calc) — 330 kbar

What I claim is:

1. As a chemical explosive, the composition of matter ammonium 2,4,5-trinitroimidazole.

* * * * *